United States Patent [19]
Laurain et al.

[11] Patent Number: 5,591,167
[45] Date of Patent: Jan. 7, 1997

[54] ANTERIOR DORSO-LUMBAR SPINAL OSTEOSYNTHESIS INSTRUMENTATION FOR THE CORRECTION OF KYPHOSIS

[75] Inventors: Jean-Marie Laurain, Pouilley les Vignes, France; Ronald L. DeWald, Chicago, Ill.; Jean-Francois D'Amore, Stella Plage; Guy Deneuvillers, Merlimont, both of France

[73] Assignee: Sofamor, S.N.C., Rang du Fliers, France

[21] Appl. No.: 452,645

[22] Filed: May 26, 1995

Related U.S. Application Data

[62] Division of Ser. No. 196,517, Feb. 15, 1994, Pat. No. 5,487,743.

[51] Int. Cl.[6] .................................................. A61B 17/56
[52] U.S. Cl. ............................................. 606/61; 606/60
[58] Field of Search .................................. 606/60, 61, 69, 606/70, 71, 90, 99, 101, 102, 105; 81/302, 318, 326, 356

[56] References Cited

U.S. PATENT DOCUMENTS

4,445,513  5/1984  Ulrich et al. .......................... 606/61
4,794,918  5/1986  Wolter ................................... 606/69
5,108,395  4/1992  Laurain ................................. 606/61
5,127,912  7/1992  Ray et al. .............................. 606/61

*Primary Examiner*—Michael Powell Buiz
*Assistant Examiner*—Mark S. Leonardo
*Attorney, Agent, or Firm*—Woodard, Emhardt, Naughton, Moriarty & McNett

[57] ABSTRACT

The instrumentation comprises a pair of vertebral implants (1) provided with screws (4) for anchorage to two corresponding vertebrae located on each side of a damaged vertebra, and a plate (3) having two end portions (3a) for connection to the two implants, and equipped with serrations (6, 15) for fixing it to the implants. The end portions (3a) of the plate have a rounded periphery and the instrumentation comprises fixing screws (50) having heads (51) which are rounded so that their surface is flush with the surface of the plate when they are anchored in the apertures of the implant and the apertures of the end portion (3a) of the plate. This arrangement ensures that the ends of the plate (3) do not come into contact with the vertebral discs when the angular position of the plate (3) relative to the implants varies, and reduces the overall size of the instrumentation.

5 Claims, 6 Drawing Sheets

ANTERIOR DORSO-LUMBAR SPINAL OSTEOSYNTHESIS INSTRUMENTATION FOR THE CORRECTION OF KYPHOSIS

This application is a division of application Ser. No. 08/196,517, filed Feb. 15, 1994, (abandoned) now U.S. Pat. No. 5,487,743.

The present invention relates to an anterior dorso-lumbar spinal osteosynthesis instrumentation and to a piston for placing this instrumentation in position, this instrumentation being adapted for the correction of kyphosis due to the destruction of one or two vertebral bodies.

There is disclosed in the French patent 89 12 187 (Publication No. 2651992) an instrumentation (termed "implant" in this patent) which comprises a pair of vertebral implants provided with screws for anchorage to two corresponding vertebrae located on each side of a damaged vertebra, and a plate having two end portions for connection to the two implants, this plate being provided with means for fixing the plate to the implants.

Now, it has been found that in certain cases the plate of this prior instrumentation undergoes a slight flexion owing to the stresses to which it is subjected, and consequently has a rigidity which is sometimes insufficient.

Further, owing to their shape, the opposite ends of the connection plate are liable to come into contact with the adjacent vertebral discs when the implants turn relative to the plate, which may slightly damage the discs by rubbing thereagainst.

Moreover, it has been found that the anchorage of the implants to the lumbar vertebrae of this prior instrumentation does not always have the desirable solidity.

Lastly, the overall thickness of this instrumentation in the region of the end portions of the plate and the implants is relatively great and it has therefore been found desirable to reduce it.

An object of the invention is to provide an instrumentation which is so arranged as to avoid these drawbacks.

According to the invention, the end portions of the plate have a rounded periphery and the means for fixing the implants to the plate are fixing screws provided with rounded heads so that their surface is flush with the surface of the plate when they are anchored in the apertures of the implant and of the associated end portion of the plate.

The rounded shape of the periphery of the end portions of the plate eliminate any projecting part which would be liable to come into contact with the vertebral discs during the relative rotations of the implants and plate. Further, the fact that the fixing screws have a surface which is flush with that of the plate when the instrumentation is placed in position on the vertebral segment, markedly diminishes the overall thickness of the instrumentation relative to the instrumentation disclosed in said patent.

According to other features of the invention:

if the instrumentation is intended for thoracic vertebral bodies, each implant is provided with two roughly diametrically opposed apertures for receiving two corresponding anchorage screws for spongy bone;

if the instrumentation is intended for lumbar vertebral bodies, each implant is provided with three apertures for receiving three anchorage screws for spongy bone. Consequently, the solidity of the anchorage in the lumbar vertebrae is very substantially improved;

the end portions of the plate are provided with apertures whose edges are conical and the end of the heads of the fixing screws has a corresponding conicity permitting a self-centring of the plate. The complementary conicities of the head of the screws and the apertures of the implants moreover reduce the overall height of the instrumentation, on one hand owing to the aforementioned flush arrangement of the surfaces of the head of the screws and the surface of the plate, and on the other hand by the avoidance of certain connection members described in said patent.

Another object of the invention is to provide a piston for placing in position two implants which are part of the considered osteosynthesis instrumentation, this piston being adapted to be handled by means of distraction or compression forceps.

Indeed, it has been found by experience that the mounting of implants by the operating method described in said patent, employing solely distraction forceps, is not always entirely satisfactory: thus, during the distraction and the compression, the vertebrae acted upon do not retain a certain freedom to rotate, which would however be desirable.

The invention therefore proposes a piston arranged in such manner as to overcome these drawbacks. According to the invention, the piston comprises in combination:

a) a first element comprising a shaft extended by a body in which is provided an annular groove for receiving a nose of a branch of the forceps, at least one radial opening for receiving a movable stud being provided in said body, b) a second element in which is formed a longitudinal cavity permitting said second element to slide on the shaft of the first element, said second element comprising a second body in which is provided an annular groove for receiving a second nose of the forceps, and at least one aperture for receiving a removable radial stud, said stud projecting from said first and second elements and being insertable in complementary apertures in the implants, c) means for adjusting the longitudinal position of the second element on the support shaft of the first element and consequently the space between the two studs respectively mounted on the first and second elements.

The two elements of the piston are allowed a limited angular movement therebetween which permits taking up a possible defective positioning of the implants.

Further, the ends of the removable studs screwed into the bodies of the two elements of the piston allow the implants freedom to rotate and consequently, in the course of the distraction and compression, they allow a certain freedom to the vertebrae being acted upon.

Further features and advantages of the invention will be apparent from the following description with reference to the accompanying drawings which illustrate two embodiments of the invention by way of non-limitative examples.

The anterior dorso-lumbar spinal osteosynthesis instrumentation according to the invention will first of all be described with reference to FIGS. 1 to 7.

The instrumentation comprises a pair of vertebral implants such as 1 (FIGS. 4 and 5) or 2 (FIGS. 6 and 7), a plate 3 (FIGS. 2 and 3) providing a connection between the two implants 1 or 2, and screws 50 for fixing the plate 3 to the two implants 1 or 2.

Figure 1:
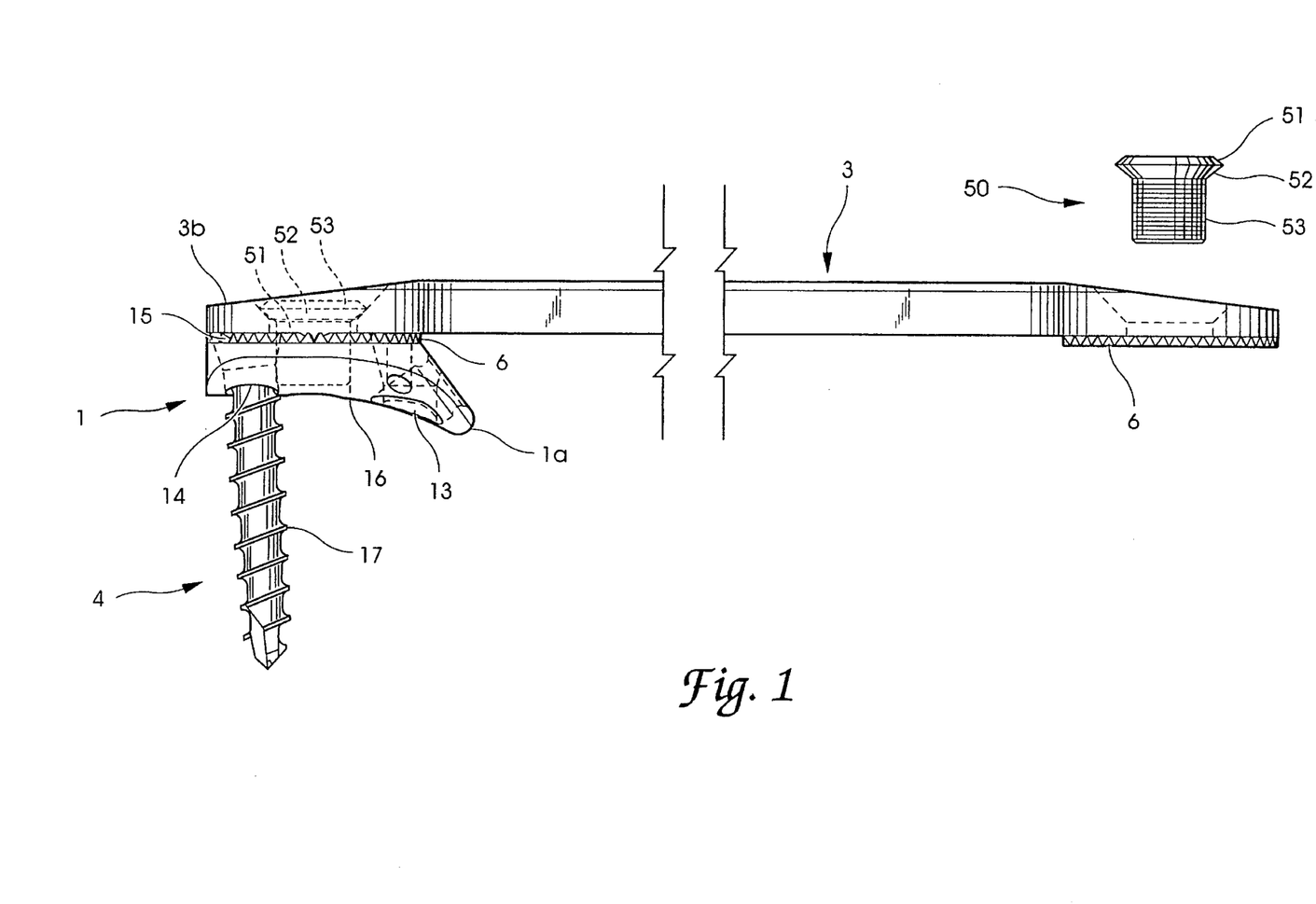
FIG. 1 is a longitudinal elevational view to a larger scale of a plate of the spinal osteosynthesis instrumentation according to the invention, one end portion of this plate being mounted on an implant and these two parts being provided with a screw which extends therethrough.
Figure 2:
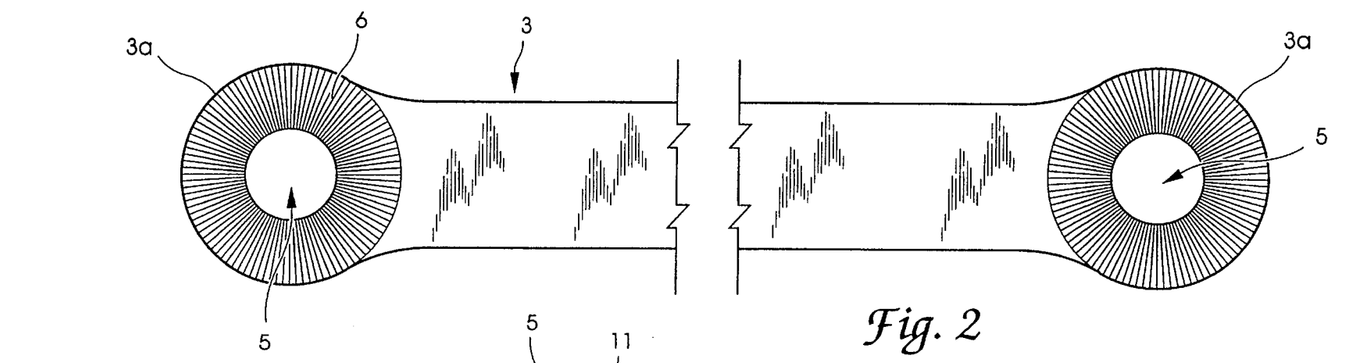
FIG. 2 is a top plan view of the plate shown in FIG. 1.
Figure 3:
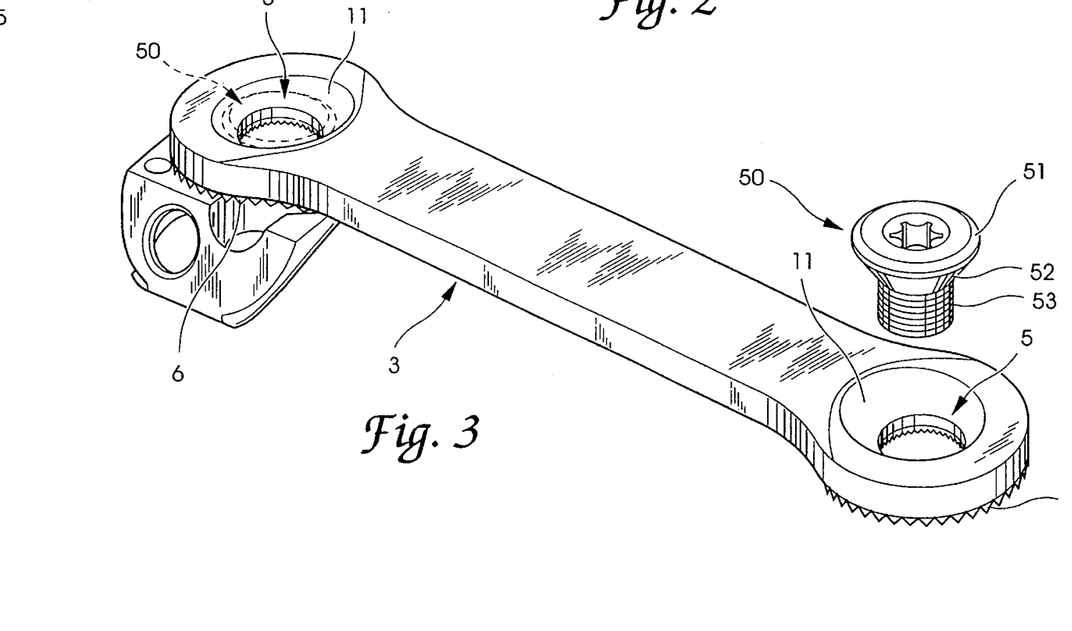
FIG. 3 is a top perspective view of the plate shown in FIGS. 1 and 2 and its screws fixing it to the implants.

The plate 3 comprises opposite end portions or heads 3a which have a rounded periphery and are provided with a central aperture 5. Provided around the aperture 5 and on the surface of the head 3a adapted to come to bear against the surface of the implants 1 or 2, are radial serrations 6 which extend to the periphery of the head 3, on a full circumference.

The fixing screws 50 have rounded heads 51 connected adjacent their screw threaded portions 53, to conical portions 52 adapted to fit into corresponding conical surfaces 11 of the apertures 5. The bone anchorage screws 4 for spongy bone each comprise a screw threaded stem 7 extended by a conical surface of a head whose surface is flush with the surface 3b of the plate 3, when the screws 4 are placed in position through the apertures 5 and central apertures 12 of the implants 1 and 2. The rounded surfaces 51 of the heads of the screws 50 are flush with the surface of the plate 3 when the screws are anchored in the apertures (12, 5) of the implants 1, 2 and the end portions 3a of the plate.

Figure 4:
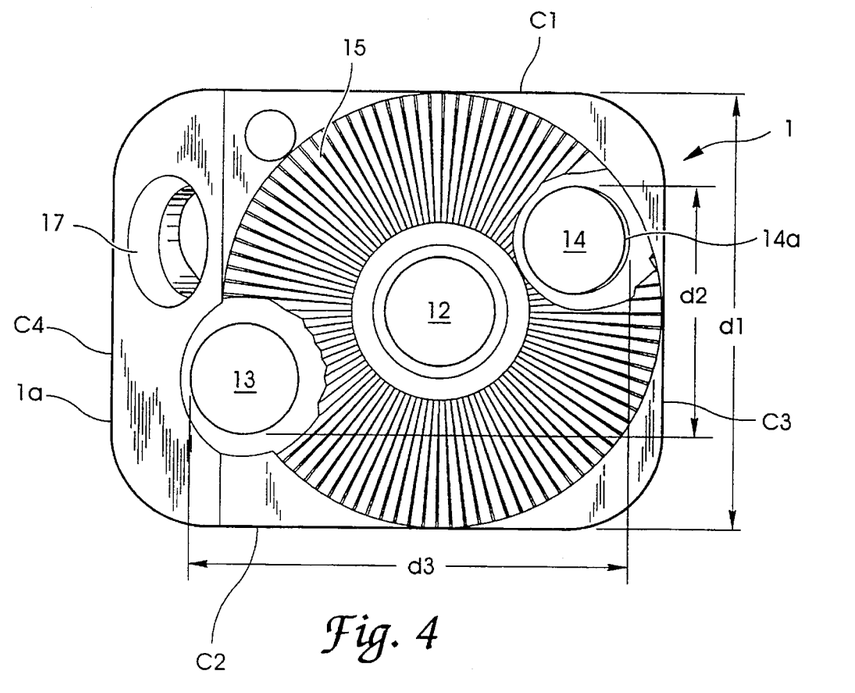
FIG. 4 is a top plan view to a larger scale of a first embodiment of an implant of the instrumentation according to the invention, this implant being intended for anchorage in thoracic vertebrae.
Figure 5:
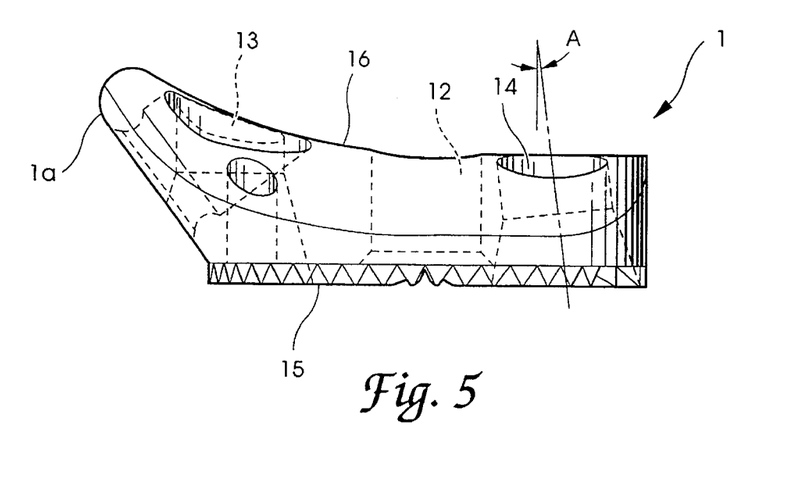
FIG. 5 is a side elevational view of the implant shown in FIG. 4.

The implant 1 is also provided with two apertures 13, 14 for receiving bone anchorage screws (not shown) on each side of the central aperture 12, and is intended especially for thoracic vertebral bodies T4 to T12. The apertures 13 and 14 are spaced apart a distance which is as small as possible so as to permit the fixing of the implant 1 on short vertebrae. The surface of the implant 1 adapted to receive the corresponding head 3a of the plate 3 has radial serrations 15 which extend completely around the aperture 12 and on each side of the apertures 13, 14. The serrations 15 of course match the serrations 6 so that the serrations fit together. The opposite surface 16 of the implant 1 has a curvature adapted to the anterior anatomy of the vertebral bodies against which the implant must be applied.

The body of the implant 1 comprises a lateral portion 1a which extends beyond the surface occupied by the serrations 15 and in which is formed an aperture 17 adapted to cooperate with the piston which will be described hereinafter with reference to FIGS. 8 to 10. The aperture 14 located on the posterior side of the vertebral implant 1 is inclined in the anterior direction of the implant at an angle which is preferably about 6°, as can be seen in FIG. 4 which shows an inclined fraction 14a of the wall of the cavity 14. On the other hand, the aperture 13 of the second screw, located on the anterior side of the implant 1, has its wall perpendicular to the upper surface of the implant 1.

The inclination of the axis of the aperture 14 toward the anterior side gives the surgeon confidence upon the insertion of the screws 4 close to the medulla canal. The fact that the aperture 13 extends in a direction perpendicular to the upper surface of the implant 1 permits an improved bone anchorage and an increased safety against risk of wrenching away.

The thickness e of the plate 3 varies in the same set of plates of different lengths in that the thickness of the plate 3 increases with increase in its distance 1 between the centres or axes of the apertures 5. This increase in thickness is determined in such manner as to provide a constant rigidity of the plate from the shortest plate to the longest plate of the set. Thus, for a set of for example 33 plates, whose centre distance 1 varies from 26 to 90 mm every 2 mm, the thickness of the plate varies progressively with the centre distance from 3 mm to 4.6 mm. The rigidity of the plate in this way remains constant irrespective of the distance between the implants 1 or 2, so that there is no risk of flexion of this plate after the instrumentation has been mounted on a patient.

Experience has shown that the most unfavorable loading resulting in an inflexion of the plate, is at more than 500 MPa, but remains lower than 600 MPa representing the yield strength of hyper hardened steel 316L, from which material the plate 3 may be advantageously made.

Further, the yield strength of cold rolled steel 316L for forging is 1,000 MPa, steel TA6V having a yield strength of 900 MPa and titanium T40 a yield strength of 340 MPa. Thus, titanium T40 cannot be employed, titanium TA6V on the other hand being well suited.

It was therefore possible to determine the rigidity of the plate from this first analysis. Then, in a manner known in the art, a rigidity was defined for the cases of previously considered loads. The data obtained is shown in the following table:

|  | STEEL | TITANIUM |
| --- | --- | --- |
| inflexion | 12 Nm/deg | 6.6 Nm/deg |
| torsion | 4.2 Nm/deg | 2.3 Nm/deg |
| flexion | 110 Nm/deg | 60 Nm/deg |
| compression | 7600 N/mm | 4200 N/mm |

This rigidity represents the plate having 90 mm between the centres or axes. In starting with the results obtained in respect of the rigidity of a plate of 90 mm, the thicknesses of the plates of a series of plates were defined with respect to their centre distance to obtain a constant rigidity, which resulted for the set of plates in a thickness variation ranging from 3 mm to 4.6 mm. As already mentioned, the two rounded heads of the plates avoid any projecting part whatever the position of these heads relative to the implants.

The lower face may comprise 48 serrations 6 arranged on 360° with a minimum pitch of 7° 30″ and a theoretical depth of 0.9 mm. The serrations of a 60° triangular shape perfectly fit into the serrations of the implants. With a half-pitch offset relative to the implant it is possible to define a "0" position in which the axis of the plate 3 is perpendicular to the axis of the implant 1 or 2. In order to avoid any projecting part, all the edges are rounded.

Figure 6:
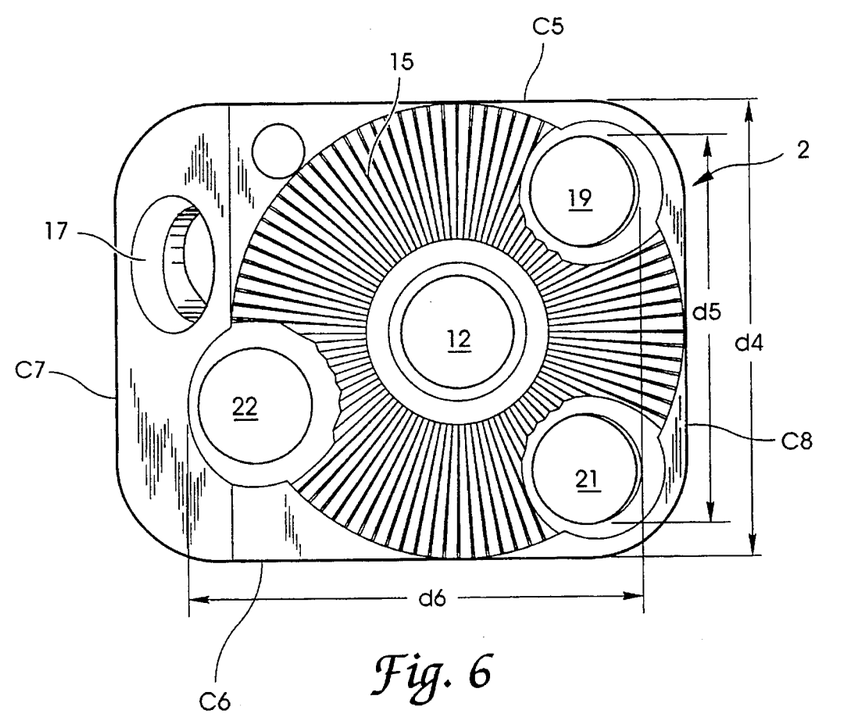
FIG. 6 is a top plan view to a larger scale of a second embodiment of an implant of the instrumentation according to the invention, this implant being intended for lumbar vertebrae.
Figure 7:
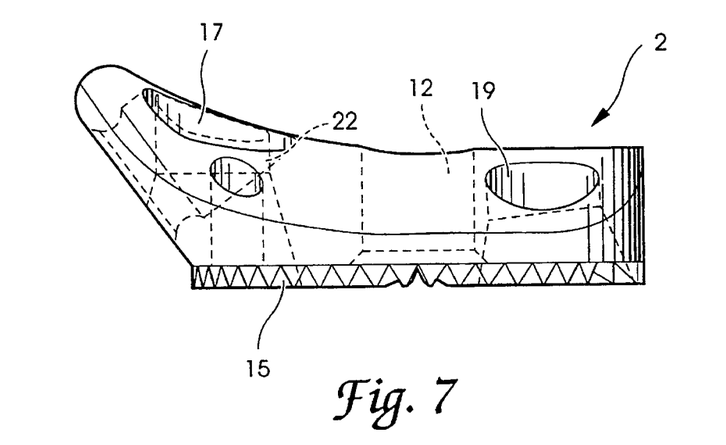
FIG. 7 is a side elevational view of the implant shown in FIG. 6.

The implant 2 is intended for lumbar vertebral bodies and is provided with three apertures 19, 21, 22 for receiving three corresponding anchorage screws for spongy bone (not shown). The walls of the apertures 19 and 21 are inclined in the anterior direction in the same way as the wall of the aperture 14, the aperture 22 being similar to the aperture 13 of the implant 1. Thus, the two apertures 19, 21 are located on the posterior side of the implant 2, and the aperture 22 is located on its anterior side.

The shape of the plate 3 has been calculated by the method of finished elements. The purpose of this calculation is to optimize the shape and the section of the plate by determining the distribution of the stresses and the rigidity of the plate. Other criteria are integrated, it being necessary for the plate to adapt itself to the anatomical morphology.

The calculations are based on the applied loads.

left-right lateral inflexion (10 Nm), torsion (3.2 Nm)

flexion (10 Nm), compression (100 daN).

The results are given in the form of Von Mists isostress volumic domains (for a 90 mm centre distance plate, the largest element in the series).

inflexion: T=587 MPa torsion: T=118 MPa flexion: T=210 MPa compression : T=97 MPa.

The overall shape of the implant was defined with respect to the morphology of the vertebral bodies.

The position of the cavities receiving the spongy bone screws was defined on the basis of documents giving the heights, diameters and thicknesses of the cortical of the vertebral bodies from T4 to L4. This led to defining two implants the screw cavities of which are at different distances apart.

Implant 1 Having Two Apertures (FIG. 4)

d1=the overall size in height, i.e. the distance between the two parallel sides C1 and C2 of the implant 1 (upper and lower sides in the drawing).

d2=the distance between the tangent to the aperture close to the side C1 and parallel to the latter and the tangent to the aperture 13 close to the side C2.

d3=the distance between the tangent to the aperture close to the posterior side C3 of the implant 1 and parallel to this side and the tangent to the aperture 13 which is the closest to the anterior side C4 of the implant.

Implant 2 Having Three Apertures (FIG. 6)

d4=the overall height of the implant according to the same definition given before, between the upper side C5 and the lower side C6 of the implant 2.

d5=the distance between the tangent to the aperture 19 close to the side C5 and parallel to the later and the tangent to the aperture 21 close to the side C6 and close to the latter.

d6=the distance between the tangent to the aperture 22 close to the anterior side C7 and parallel to the latter and the tangent to the aperture 21 close to the posterior side C8 and parallel to the latter.

The maximum distances d2, d3, d5, d6 are given in the following table as a function of the minimum and maximum heights of the vertebral bodies. The overall height d1 may vary from 13.7 to 20 mm and the overall size d4 of the implant 2 may vary from 20 to 32 mm.

|  | Implant-2 apertures (1) | Implant-3 apertures (2) |
| --- | --- | --- |
| Maximum distance d2 | 11.5 mm |  |
| Maximum distance d3 | 20.2 mm |  |
| Maximum distance d5 |  | 17 mm |
| Maximum distance d6 |  | 20 mm |
| Vertebral body height | 13.7 mm min | 32 mm max |

If the height of the vertebra is between 13.7 mm and 20 mm, an implant 1 having two apertures is used. If this height is between 20 and 32 mm, an implant 2 having three apertures is used.

A minimum distance between the screws toward the interior is very important since it must be ensured that the screws are not too close together so as to avoid risk of splitting the cortical.

The cavities (14, 19, 21) for the screws at the rear of the implant (1, 2) are inclined at 6° toward the interior for two reasons:

1) give confidence to the surgeon when mounting the implant as the inclination avoids the medulla canal, 2) relative to the anterior screw, the assembly forms a triangular mounting ensuring an improved resistance to traction.

The 6° were defined by the fact that it was necessary to ensure that the longest screws do not touch each other when passing through the other cortical, and that they are spaced far enough apart to avoid splitting the other cortical, which would result in an imperfect fixing of the implant.

As the adjustment between the screw and its cavity is very precise, it is possible to avoid the anchorage points as found on a known implant, which are liable to result in fractures and dangerous asperities for the organism.

The choice was therefore made to retain a smooth surface in contact with the bone by permitting the anchorage owing to the absence of clearance between the screw and the implant.

Figure 8:
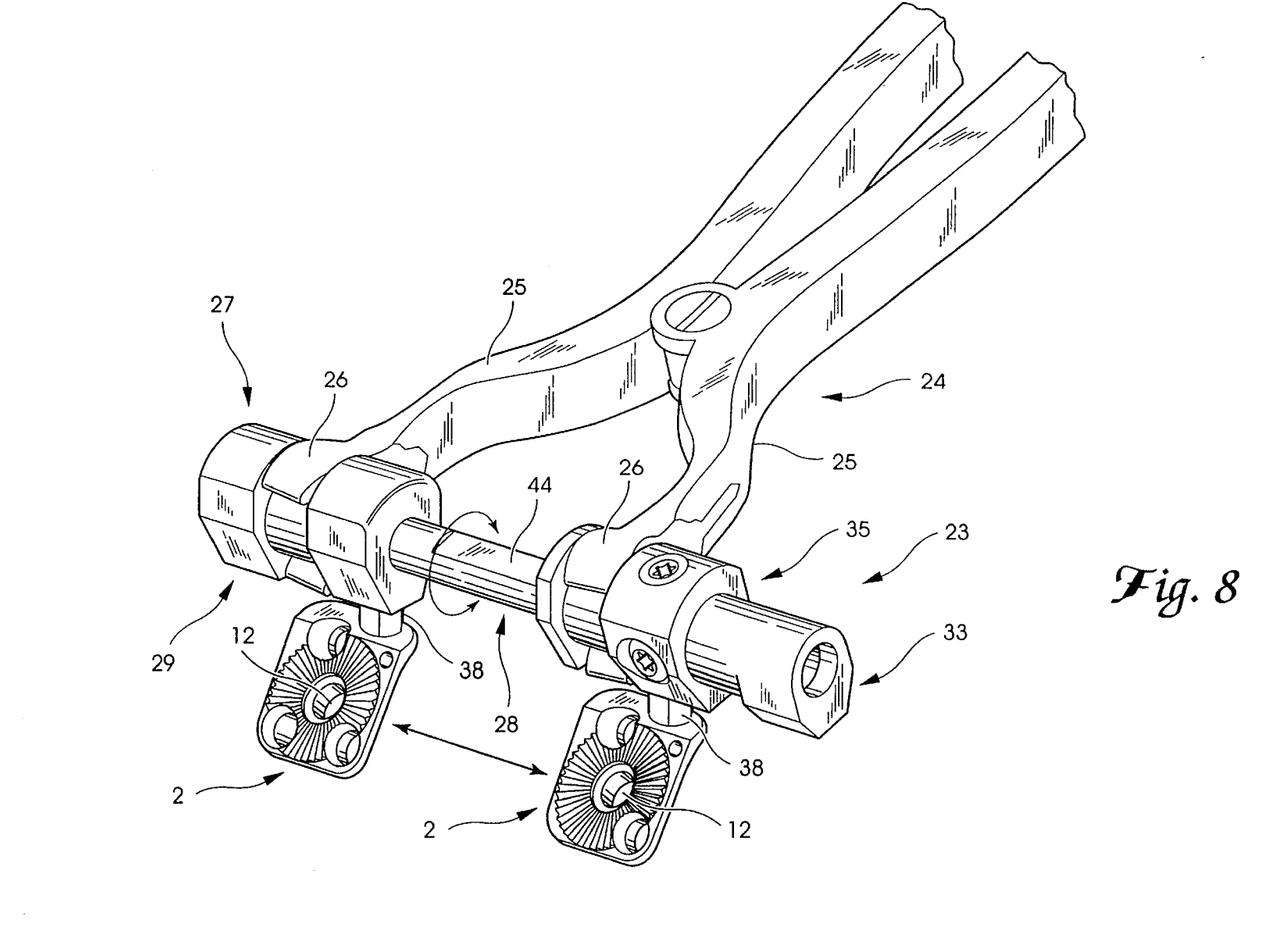
FIG. 8 is a perspective view of a device comprising an embodiment of the piston according to the invention, two implants connected to the corresponding studs of this piston, and distraction forceps the noses of which are engaged in the annular grooves of the piston.
Figures 9, 10:
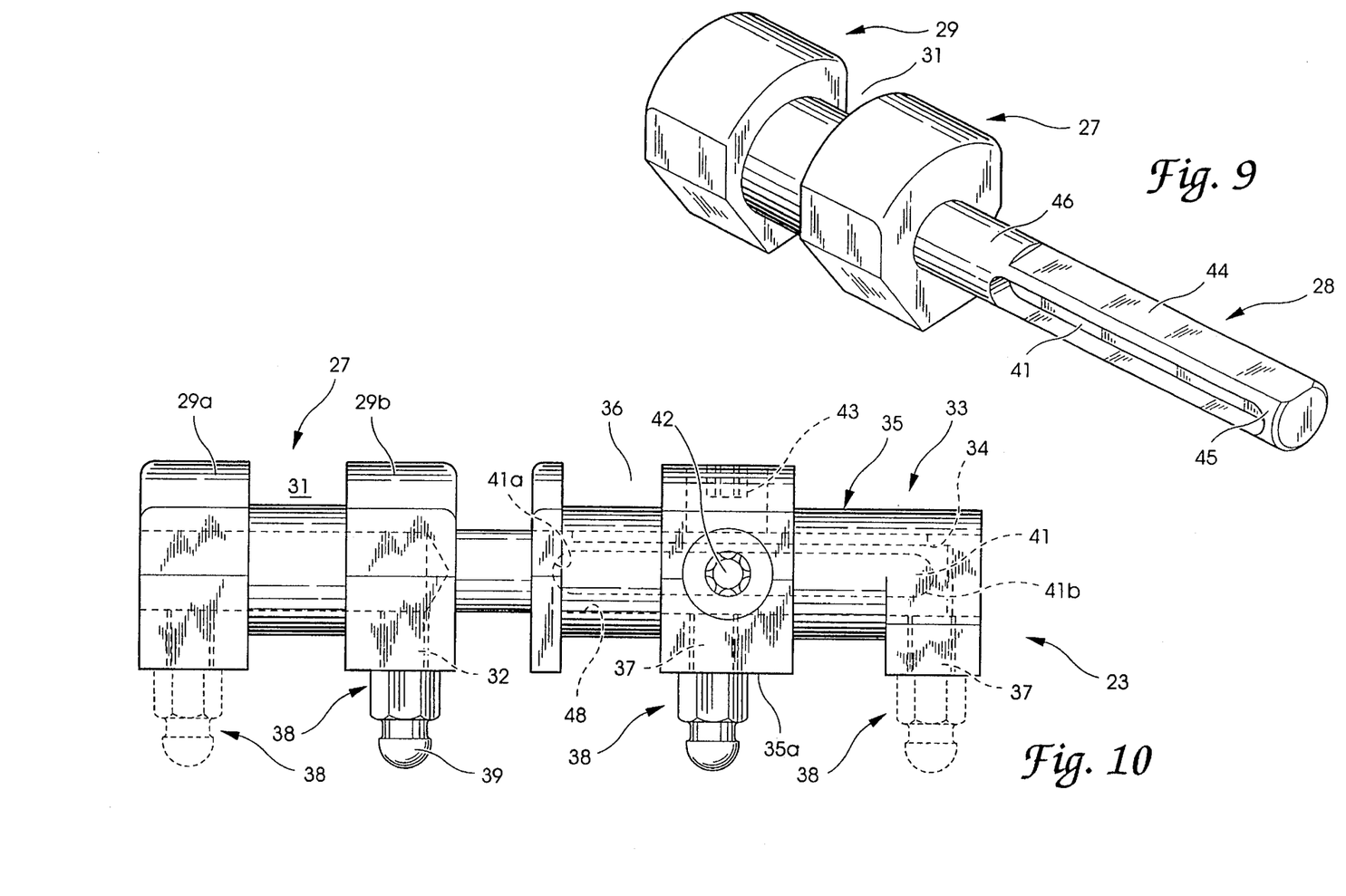
FIG. 9 is a perspective view of the part of the piston shown in FIG. 8 provided with a shaft supporting the other part.
FIG. 10 is a longitudinal elevational view to a larger scale of the piston shown in FIG. 8, the second element being moved closer to the first element.

Description of the Piston 23 (FIG. 8 to 10)

The piston 23 is adapted to permit the mounting of two implants 1 or 2 adapted for handling with distraction or compression forceps 24, each branch 25 of which terminates in a nose 26.

The piston 23 comprises the following component parts:

a) A first element 27 having a shaft 28 extended by a body 29 in which is formed an annular groove or recess 31 dimensioned to receive a nose 26; at least one radial opening 32, namely two openings in the illustrated embodiment, are formed in the two parts 29a, 29b of the body 29 on each side of the groove 31.

b) A second element 33 in which is formed a longitudinal cavity 34 in which the shaft 28 is slidable so that the element 33 is slidable on the shaft 28. The second element 33 comprises a second body 35 in which are provided an annular groove 36 for receiving the second nose 26 of the forceps 24, and at least one aperture 37, namely in the illustrated embodiment two radial apertures 37 for receiving corresponding studs 38. The apertures 37 and the apertures 32 may be for example tapped for receiving screw threaded studs 38 having a spherical head 39 which project from the bodies 29 and 35 after insertion in their respective apertures 32, 37. The spherical end heads 39 are adapted to be inserted in corresponding apertures 17 of the implants 1 or 2 (FIG. 8).

c) Means for adjusting the longitudinal position of the second element 33 on the support shaft 28, and consequently the distance between two studs 38 respectively mounted on the elements 27 and 33 in two of the apertures 32, 37 spaced apart a distance corresponding to that between the implants 1 or 2.

In the illustrated embodiment, the aforementioned means comprise a longitudinal slot 41 provided in the shaft 28, close at its opposite ends and open laterally on at least one side, a lateral pin 42, which extends through the second element 33, having an end portion slidably engaged in this slot 41. Thus, during the movements in translation of the element 33 on the shaft 28, the pin 42 can abut against either one of the ends 41a, 41b of the slot 41 and thereby limit the travel of the element 33 on the element 27. Lastly, the means for providing a relative adjustment of the two elements 33, 27 are completed by a device for clamping the two elements in a predetermined relative position. In the embodiment illustrated in FIG. 10, this device is formed by a screw 43 engaged in a radial opening in the central part 35a of the body 35 so as to be capable of entering the slot 41 and coming to bear against a longitudinal flat surface 44 on the shaft 28 and thereby clamping the second element 33 in the chosen position on the shaft 28.

The lateral pin 42 may be a spigot screw whose spigot is slidable in the longitudinal slot 41. It will be understood that the four tapped apertures 32, 37 are in alignment so as to be capable of being positioned on the implants 1 or 2, two studs 38 being respectively inserted in the elements 27 and 33, each one in either one of the two apertures 32, 37 in accordance with the distance between the two implants 1 or 2 and therefore with the centre distance of the corresponding plate 3. Thus, in the embodiment shown in FIG. 10, two studs 38 are placed in the apertures 32, 37 which are the closest to each other. The maximum distance apart corresponds to a position in which the pin 42 abuts against the end 41b of the slot 41 and in which the studs 38 are respectively inserted in the apertures 32, 37 which are spaced the greatest distance apart.

The body 35 of the second element 33 has a length exceeding that of the body 29 of the first element 27 and the annular groove 36 of the second body 35 is axially offset toward the body 29 of the element 27 so as to constitute an asymmetric piston. Further, on each side of the longitudinal flat surface 44 and between one end of the latter and the part 29b of the body 29, the surface of the shaft 28 has cylindrical bearing surfaces 45 and 46 which are complementary to a cylindrical internal surface 48 of the longitudinal cavity 34 of the second element 33. This arrangement permits a relative rotation of the two elements 27 and 33 in addition to their freedom of movement in translation relative to each other (arrows shown in FIG. 8).

The forceps 24 and the piston 23 are temporarily interconnected by means of an indexing system with the use of a ball retained by a spring, these elements being known per se and not shown. This system permits retaining the piston 23 between the branches or jaws 25 of the forceps 24 while allowing the separation of the two elements without creating large stresses liable to hinder the utilization of the piston.

This manner of fixing permits retaining a freedom of rotation of the forceps 24 around the shaft 28 of the piston 23, which clears the operating field and permits positioning the piston 23 upon the insertion of the studs 38 in the implants 1 or 2. The pair of forceps 24 is equipped with a rack (not shown) known per se which enables the piston 23 to be temporarily clamped in position.

Thus the device for operating the piston 23 comprises two forceps, namely distraction forceps and compression forceps. This system is based on the condition according to which, whether the action be distraction or compression, the surgeon effects the same movement, i.e. a compression of the hand which enables him to feel very well, by the pressure exerted, the force applied to the piston 23.

Apart from the aforementioned advantages, the last-mentioned advantage has further advantages: for a defined and constant curve, the piston may be used in all of the existing centre distance variations (from 22 mm to 100 mm). The relative freedom of rotation allowed the two elements 27, 33 of the piston 23 during its use, leaves a certain amount of freedom to the vertebrae being acted upon in the course of the distraction and the compression.

The asymmetry of the piston 23 also affords the following advantages: with the moving part, constituted by the second element 33, longer than the "fixed" part 27, and with the groove or recess 36 for connecting the associated forceps 24 offset toward the central part of the piston 23, it is possible for the surgeon to work under the ribs. Further, this asymmetry, combined with the release of the forceps 24 from the piston 23, permits working in all positions, and the piston 23 can be used just as well by a right-handed person and a left-handed person.

The surgical method of mounting the instrumentation just described, by means of the piston 23 and forceps such as the forceps 24, is the following:

two respective implants 1 or 2 are placed in position on two vertebrae located on each side of a damaged vertebra by means of anchorage screws of the spongy bone type (described in particular in the aforementioned French patent);

two studs 38 of the piston 23 are inserted in the corresponding apertures 17 of the implants 1 or 2;

the noses 26 of the branches 25 of the forceps 24 are engaged on the piston 23 at the places provided for this purpose, i.e. in the grooves 31 and 36, the second element 33 being freely slidable on the shaft 28;

a slight upper distraction is effected by opening the forceps 24;

a graft is placed in position between the two implants 1 or 2;

the forceps 24 are released so that the piston 23 returns to its initial position;

the forceps are interchanged so as to use the compression forceps (not shown in the drawings and known per se), and the implants 1 or 2 are moved closer together by means of the compression forceps and with compression of the two adjacent vertebrae;

the distance between the two implants 1 or 2 is measured;

the piston 23 is clamped in this position by immobilizing its two elements 27 and 33 with respect to each other;

the plate 3 of corresponding length is chosen and is placed in position on the two implants 1 or 2 and the mounting is terminated by insertion of the fixing screws in the apertures 5 and 12 of the plate 3 and the implants.

Many alternative embodiments of the invention may be envisaged. Thus, it is for example clear that the means for adjusting the relative position of the elements 27 and 33 of the piston 23 may be different from those (42, 43) shown, the same being true of the arrangement of the studs 38.

What is claimed is:

1. A piston assembly for placing in position two implants forming part of an anterior dorso-lumbar spinal osteosynthesis instrumentation, usable with forceps having two branches and first and second noses at the respective ends of said branches, comprising:

a first element including a body, a shaft extending from said body, an annular groove defined in said body for receiving a first nose of one branch of the forceps, and at least one radial aperture defined in said body;

a second element, longitudinal cavity defined in said second element permitting said second element to slide on said shaft of said first element, said second element including a second body, an annular groove defined in said second body for receiving a second nose of another branch of the forceps, and at least one aperture defined in said second body;

a pair of studs removably mountable within an aperture in a corresponding one of said first and second elements, said studs projecting from said first element and said second element and being insertable in complementary apertures in the two implants; and means for limiting the relative longitudinal position of said body of said second element on said shaft and consequently the distance between said studs respectively mounted in said apertures of said first element and said second element.

2. A piston assembly for placing in position two implants forming part of an anterior dorso-lumbar spinal osteosynthesis instrumentation, usable with forceps having two branches and first and second noses at the respective ends of said branches, comprising:

a first element including a body, a shaft extending from said body, an annular groove defined in said body for receiving a first nose of one branch of the forceps, and at least one radial aperture defined in said body;

a second element, longitudinal cavity defined in said second element permitting said second element to slide on said shaft of said first element, said second element including a second body, an annular groove defined in said second body for receiving a second nose of another branch of the forceps, and at least one aperture defined in said second body;

a pair of studs removably mountable within aperture in a corresponding one of said first and second elements, said studs a projecting from said first element and said second element and being insertable in complementary apertures in the two implants; and means for limiting the relative longitudinal position of said body of said second element on said shaft and consequently the distance between said studs respectively mounted in said apertures of said first element and said second element, wherein said means for limiting the relative longitudinal position of said second element on said shaft includes;

a longitudinal slot defined in said shaft, said slot being closed at its ends and laterally open on at least one side, a lateral pin attached to said second element slidably engaged in said slot so as to abut against either end of said slot to limit the travel of said second element on said first element, and means for clamping said first and second elements together in a predetermined relative position.

3. The piston assembly according to claim 2, wherein said means for clamping includes a lateral tapped aperture defined in said second element, and a screw threadedly engageable in said lateral tapped aperture and tightenable against said shaft of said first element to thereby clamp said first and second elements relative to each other.

4. The piston assembly according to claim 1, wherein when said second element if slidably received on said shaft of said first element said annular groove of said second element is axially offset toward said body of said first element relative to said aperture defined in said second body, and said annular groove of said first element if axially offset away from said second body relative to said aperture defined in said first body so as to constitute an assymetric piston.

5. The piton assembly according to claim 1, wherein said longitudinal cavity in said second element has an internal cylindrical surface, and said shaft of said first element defines two cylindrical bearing surfaces complementary to said internal cylindrical surface so as to permit a relative rotation between said first element and said second element.

* * * * *